(12) United States Patent
Takagi

(10) Patent No.: US 8,254,522 B2
(45) Date of Patent: Aug. 28, 2012

(54) DYNAMIC IMAGE CAPTURING CONTROL APPARATUS AND DYNAMIC IMAGE CAPTURING SYSTEM

(75) Inventor: Tatsuya Takagi, Tokyo (JP)

(73) Assignee: Konica Minolta Medical & Graphic Inc., Tokyo (JP)

( * ) Notice: Subject to any disclaimer, the term of this patent is extended or adjusted under 35 U.S.C. 154(b) by 106 days.

(21) Appl. No.: 12/992,158

(22) PCT Filed: Feb. 19, 2009

(86) PCT No.: PCT/JP2009/052899
§ 371 (c)(1),
(2), (4) Date: Nov. 11, 2010

(87) PCT Pub. No.: WO2009/139206
PCT Pub. Date: Nov. 19, 2009

(65) Prior Publication Data
US 2011/0064201 A1    Mar. 17, 2011

(30) Foreign Application Priority Data

May 14, 2008    (JP) ................................. 2008-126634

(51) Int. Cl.
    *H05G 1/60*    (2006.01)
(52) U.S. Cl. ...................................................... 378/95
(58) Field of Classification Search .................... 378/95, 378/96, 97, 23
    See application file for complete search history.

(56) References Cited

U.S. PATENT DOCUMENTS

| 7,349,522 B2 * | 3/2008 | Yan et al. .................. 378/65 |
| 7,471,767 B2 * | 12/2008 | Spahn ........................ 378/95 |
| 2004/0223587 A1 | 11/2004 | Tsujii |
| 2005/0243967 A1 | 11/2005 | Inoue |
| 2006/0104417 A1 | 5/2006 | Kameshima et al. |
| 2007/0040099 A1 | 2/2007 | Yokoyama et al. |
| 2007/0189436 A1 | 8/2007 | Goto et al. |

(Continued)

FOREIGN PATENT DOCUMENTS

JP    6-189947 A    7/1994

(Continued)

OTHER PUBLICATIONS

International Search Report dated Jun. 2, 2009 issued in International Appln. No. PCT/JP2009/052899.

*Primary Examiner* — Irakli Kiknadze
(74) *Attorney, Agent, or Firm* — Holtz, Holtz, Goodman & Chick, PC

(57) ABSTRACT

A dynamic image, of a quality required for diagnosis that does not increase the radiation dosage of a person being imaged, can be captured by a dynamic imaging system that includes an imaging console which has a control unit. The control unit analyzes at least one of the frame images captured at an initial state of dynamic imaging, calculates an index indicating the quality of the image, and calculates, by using the calculated index, an upper limit frame rate $f_{sup}$ such that the index indicating the quality of the frame image captured by the dynamic imaging is below a determined reference value. The frame rate used for dynamic imaging is determined according to the calculated upper limit frame rate $f_{sup}$ and a lower limit frame rate $f_{inf}$ required to diagnose the dynamic state of the imaged region. An imaging device may image the person at the determined frame rate.

6 Claims, 10 Drawing Sheets

U.S. PATENT DOCUMENTS

2008/0221442 A1 * 9/2008 Tolkowsky et al. ........... 600/425

FOREIGN PATENT DOCUMENTS

| | | |
|---|---|---|
| JP | 2004-325251 A | 11/2004 |
| JP | 2004-325261 A | 11/2004 |
| JP | 2005-245761 A | 9/2005 |
| JP | 2005-312775 A | 11/2005 |
| JP | 2006-68512 A | 3/2006 |
| JP | 2006-158728 A | 6/2006 |
| JP | 2007-18379 A | 1/2007 |
| JP | 2007-75598 A | 3/2007 |
| WO | WO 2005/122901 A1 | 12/2005 |

* cited by examiner

DYNAMIC IMAGE CAPTURING CONTROL APPARATUS AND DYNAMIC IMAGE CAPTURING SYSTEM

This application is a U.S. National Phase Application under 35 USC 371 of International Application PCT/JP2009/052899 filed Feb. 19, 2009.

TECHNICAL FIELD

The present invention relates to a dynamic image capturing control apparatus and a dynamic image capturing system.

BACKGROUND ART

In the field of medicine, lately, instead of capturing and diagnosis of a still image with radiation using a conventional film/screen or photostimulable phosphor plate, there is an attempt to capture a dynamic image of an object using a semiconductor image sensor such as a FPD (flat panel detector), etc. and to apply this in diagnosis. Specifically, speed of responsiveness of reading and deleting of image data of the semiconductor image sensor is used to successively emit pulsed radiation from a radiation source at a timing of reading and deleting of the semiconductor image sensor to perform a plurality of capturing per second to capture an object dynamically. By sequentially displaying a series of the plurality of images obtained by the capturing, a doctor is able to recognize a series of movement of the capturing body part.

In dynamic capturing, since capturing is performed a plurality of times, if the same amount of radiation as still image capturing is emitted in each capturing, amount of radiation exposure of the object becomes a considerable amount. Therefore, for example, patent document 1 describes a technique of dynamic capturing to suppress a total of emitted radiation in dynamic capturing to an amount equal to or less than that of still image capturing.

Patent Document 1: Japanese Patent Application Laid-Open Publication No. 2005-312775

DISCLOSURE OF THE INVENTION

Problems to be Solved by the Invention

However, in the patent document 1, when a number of frames to be captured is set to a high number, the emission radiation amount with respect to each image decreases and image quality of each image decreases and image quality necessary for image analysis and diagnosis may not be achieved. Alternatively, if the emission radiation amount of a total dynamic capturing is increased, the decrease of image quality can be prevented but the amount of radiation exposure of the object increases.

An object of the present invention is to obtain a dynamic image with image quality demanded for diagnosis without increasing radiation exposure amount of an object.

Means for Solving the Problem

In order to achieve the above object, according to a first aspect of the present invention, there is provided a dynamic image capturing control apparatus connected to a capturing apparatus in which dynamic capturing is performed by successively emitting radiation on a capturing body part a plurality of times to obtain a plurality of frame images showing a dynamic state of the capturing body part, the dynamic image capturing control apparatus including:

an operation section to specify the capturing body part which is to be a capturing object;

a capturing control section to set in the capturing apparatus a capturing condition including emission radiation amount and frame rate used in the dynamic capturing according to the capturing body part specified by the operation section to perform the dynamic capturing to obtain a plurality of frame images showing the dynamic state of the capturing body part;

an index value calculation section to analyze at least one frame image obtained by the capturing device before the actual dynamic capturing to calculate an index value showing image quality;

an upper limit frame rate calculation section to calculate an upper limit of the frame rate so that the index value showing image quality of the each frame image obtained by the actual dynamic capturing is no more than a predetermined standard value based on the calculated index value showing the image quality, wherein the capturing control section determines the frame rate to be used in the actual dynamic capturing based on the calculated upper limit frame rate and allows the capturing apparatus to perform the actual dynamic capturing at the determined frame rate.

Preferably, in the dynamic image capturing control apparatus, the index value showing the image quality is a noise level of the frame image;

the index value calculating section sets an area of interest in the frame image obtained by the capturing device, extracts a non-edge area in the area of interest and calculates a local dispersion value of an image signal component of a high frequency range in the extracted non-edge area to calculate the noise level of the frame image.

Preferably, the dynamic image capturing control apparatus, further includes:

a storage section to store a lower limit frame rate necessary for diagnosis of the dynamic state of the capturing body part with respect to each capturing body part; and a notification section to read out the lower limit frame rate according to the capturing body part specified on the operation section from the storage section to compare the calculated upper limit frame rate to the read out lower limit frame rate and to notify the result when the upper limit frame rate is lower than the lower limit frame rate as a result of the comparison.

Preferably, in the dynamic image capturing control apparatus, the dynamic state of the capturing body part is a dynamic state with a cyclic nature; and the capturing control section allows the capturing apparatus to perform the actual dynamic capturing at the lower limit frame rate when the upper limit frame rate is lower than the lower limit frame rate, and the dynamic image capturing control apparatus further comprises a noise reduction processing section to perform noise reduction processing by performing averaging of pixel signal values among frame images of a plurality of cycles of the dynamic state of the capturing body part obtained by the actual capturing.

Preferably, in the dynamic image capturing control apparatus, a cycle number determination section to calculate the index value showing image quality of the frame image obtained by performing the dynamic capturing at the lower limit frame rate and to determine a dynamic cycle number of the body part used in the noise reduction processing based on the calculated index value showing the image quality, wherein the noise reduction processing section performs noise reduction processing by performing averaging of pixel signal values among frame images of the determined dynamic cycle number among a plurality of frame images obtained by the actual capturing.

According to a second aspect of the present invention, there is provided a dynamic image capturing system including:

an operation section to specify the capturing body part which is to be a capturing object;

a capturing section to perform dynamic capturing by successively emitting radiation on the specified capturing body part a plurality of times to obtain a plurality of frame images showing a dynamic state of the capturing body part;

a capturing control section to set in the capturing section a capturing condition including emission radiation amount and frame rate used in the dynamic capturing according to the capturing body part specified by the operation section to perform the dynamic capturing;

an index value calculation section to analyze at least one frame image obtained by the capturing device before the actual dynamic capturing to calculate an index value showing image quality;

an upper limit frame rate calculation section to calculate an upper limit of the frame rate so that the index value showing image quality of the each frame image obtained by the actual dynamic capturing is no more than a predetermined standard value based on the calculated index value showing the image quality, wherein the capturing control section determines the frame rate to be used in the actual dynamic capturing based on the calculated upper limit frame rate and allows the capturing section to perform the actual dynamic capturing at the determined frame rate.

Advantageous Effect of the Invention

According to the present invention, a dynamic image with image quality demanded in diagnosis can be obtained without increasing a radiation exposure amount of the object.

BEST MODE FOR CARRYING OUT THE INVENTION (Configuration of Dynamic Image Capturing System 100)

First, the configuration is described.

Figure 1:
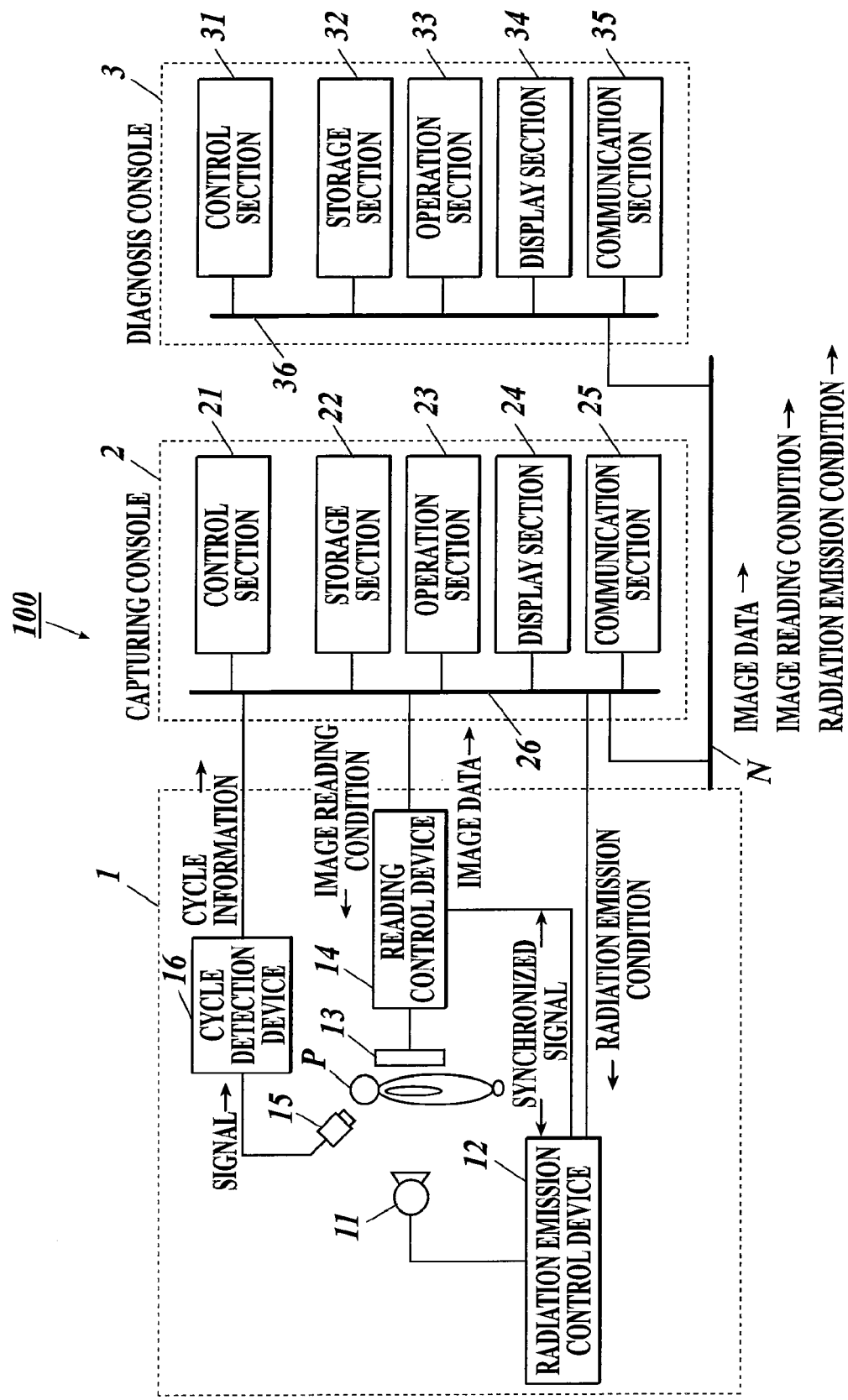
FIG. 1 is a diagram showing an example of an entire configuration of a dynamic image capturing system according to an embodiment of the present invention.

FIG. 1 shows an entire configuration of a dynamic image capturing system 100 of the first embodiment.

As shown in FIG. 1, the dynamic image capturing system 100 is composed of a capturing device 1 and a capturing console 2 connected by a communication cable, etc. and a capturing console 2 and diagnosis console 3 connected through a communication network N such as a LAN (Local Area Network), etc.

(Configuration of Capturing Device 1)

The capturing device 1 is a capturing section to capture a dynamic state of a human body with a cycle such as change in form of lungs expanding and contracting with breathing, beating of the heart, etc. Dynamic capturing is performed by obtaining a plurality of images by successively emitting radiation (in other words successive capturing) on a capturing body part of an object. A series of images obtained by the successive capturing is called a dynamic image. Also, the plurality of images composing a dynamic image are each called a frame image.

As shown in FIG. 1, the capturing device 1 includes a radiation source 11, a radiation emission control device 12, a radiation detection section 13, a reading control device 14, a cycle detection sensor 15, a cycle detection device 16, and the like.

The radiation source 11 emits radiation (X-ray) to a patient P according to control by the radiation emission control device 12.

The radiation emission control device 12 is connected to the capturing console 2 and controls the radiation source 11 based on a radiation emission condition input from the capturing console 2 to perform radiation capturing. The radiation emission condition input from the capturing console 2 includes, for example, pulse rate, pulse width, pulse interval, timing of start/end of capturing, cycle number of capturing, value of X-ray tube current, value of X-ray tube voltage, filter type, etc. in successive emission. The pulse rate is a number of radiation emission with respect to each unit of time (here, with respect to each second) and matches a later described frame rate. The pulse width is radiation emission time with respect to each emission of radiation. The pulse interval is time from the start of one radiation emission to the start of the next radiation emission in successive capturing and matches a later described frame interval.

The radiation detection section 13 is composed of a semiconductor image sensor such as a FPD. The FPD includes, for example, a glass substrate, etc. and detects the radiation emitted from the radiation source 11 to a predetermined position on the substrate and transmitted at least through a capturing body part of the patient P according to intensity of the radiation and converts the detected radiation to an electric signal to align the accumulated plurality of pixels in a matrix shape. Each pixel is composed of a switching section such as, for example TFT (Thin Film Transistor), etc.

The reading control device 14 is connected to the capturing console 2. The reading control device 14 controls the switching section of each pixel of the radiation detection section 13 based on an image reading condition input from the capturing console 2 to switch reading of the electric signal accumulated in each pixel. The electric signal accumulated in the radiation detection section 13 is read to obtain image data. Then, the obtained image data is output to the capturing console 2. The image reading condition includes, for example, frame rate, frame interval, pixel size, image size (matrix size), etc. The frame rate is a number of frame images obtained with respect to each unit of time (here, with respect to each second) and matches the pulse rate. The frame interval is time from the start of obtaining operation of one frame image to the start of the obtaining operation of the next frame image in successive capturing and matches the pulse interval.

The pulse interval and frame interval is obtained from the pulse rate and the frame rate.

Here, the radiation emission control device 12 and the reading control device 14 are connected to each other and send and receive a synchronized signal to each other to synchronize operation of radiation emission and operation of reading the image.

The cycle detection sensor 15 detects status of the capturing body part of the patient P and outputs detection information to the cycle detection device 16. As the cycle detection sensor 15, for example, when the capturing body part is the lungs (inspiring and expiring), a breathing monitor belt, a CCD (Charge Coupled Device) camera, an optical camera, a spirometer, etc. can be applied. Also, when the capturing body part is the heart (blood current), an electrocardiograph, etc. can be applied.

Based on the detection information input from the cycle detection sensor 15, the cycle detection device 16 detects the cycle number of a dynamic state of the capturing body part (Cycle number with respect to each unit of time. For example, when the capturing body part is the lungs (inspiring and expiring), the breathing rate (times/second) and when the capturing body part is the heart, the heart rate (times/second)), which state of the cycle the status of the capturing body part is in at present, etc. is detected and the detection result (cycle information) is output to the control section 21 of the capturing console 2.

For example, in a case where the capturing body part is the lungs (inspiring and expiring), when the cycle detection sensor 15 (breathing monitor belt, CCD camera, optical camera, spirometer etc.) inputs detection information showing the state of the lungs is at a point of changing from inspiring to expiring, the cycle detection device 16 sets the input timing as a base point of one cycle and recognizes the interval until the next timing that this state is detected as one cycle.

Also, in a case where the capturing body part is the heart (including blood current), when the cycle detection sensor 15 (electrocardiograph, etc.) inputs R wave, the cycle detection device 16 sets the input timing as a base point and recognizes the interval until the next timing that the R wave is detected as one cycle.

The cycle number recognized with respect to each second is detected as the cycle number.

(Configuration of Capturing Console 2)

The capturing console 2 is a dynamic image capturing control device to set the radiation emission condition and the image reading condition in the capturing device 1 to control the radiation capturing and the reading operation of the radiation image by the capturing device 1 and is also a device to display the dynamic image obtained by the capturing device 1 for confirmation by the capturing operator.

As shown in FIG. 1, the capturing console 2 includes, a control section 21, a storage section 22, an operation section 23, a display section 24, a communication section 25 and the like, and each section is connected to each other through a bus 26.

The control section 21 is composed of a CPU (Central Processing Unit), RAM (Random Access Memory), etc. According to an operation of the operation section 23, the CPU of the control section 21 reads out a system program or various programs stored in the storage section 22 and expands the program in the RAM. According to the expanded program, the control section 21 centrally controls the operation of each section of the capturing console 2 and the radiation emission operation and the reading operation of the capturing device 1.

Specifically, the control section 21 reads out the capturing control processing program stored in the storage section 22 and performs the capturing control processing to realize functions as a capturing control section, upper limit frame rate calculation section, noise reduction processing section and cycle number determination section. Also, the control section 21 reads out the noise level calculation processing program stored in the storage section 22 and performs the noise level calculation processing to realize a function as an index value calculation section.

The storage section 22 is composed of a nonvolatile semiconductor memory, hard disk, etc. The storage section 22 stores various programs performed by the control section 21, parameter necessary to perform processing by the program, or data such as processing result, etc. The various programs are stored in a form of a readable program code and the control section 21 sequentially performs the operation according to the program code.

For example, the storage section 22 stores a capturing control processing program to perform a later described capturing control processing. Also, the storage section 22 stores a capturing condition (radiation emission condition and image reading condition) according to the capturing body part with respect to each capturing body part. As a capturing condition stored in the storage section 22 with respect to each capturing body part, there are, for example, frame rate (pulse rate), timing of start/end of capturing, capturing cycle number, value of X-ray tube current, value of X-ray tube voltage, total emission radiation amount, pixel size, image size, etc. Such capturing condition with respect to each capturing body part is obtained experimentally and empirically and is set based on typical dynamic cycle time of each capturing body part (time necessary with respect to each cycle), frame image number of each cycle necessary for diagnosis, allowable radiation exposure amount, etc.

Also, the storage section 22 stores the lower limit frame rate $f_{inf}$ determined in advance according to the capturing body part with respect to each capturing body part. The lower limit frame rate $f_{inf}$ is the frame rate set as the necessary lower limit to diagnose the dynamic state of the capturing body part. The value is obtained experimentally and empirically and is calculated based on cycle number with respect to each unit of time of the capturing body part, frame image number with respect to each cycle necessary for diagnosis, etc.

The operation section 23 is composed of a keyboard including a cursor key, number input key, various function keys, etc., and a pointing device such as a mouse, etc. and outputs an instruction signal input by operation of the key on the keyboard or operation of the mouse to the control section 21. The operation section 23 can include a touch panel on the display screen of the display section 24, and in this case, the instruction signal input through the touch panel is output to the control section 21.

The display section 24 is composed of a monitor such as an LCD (Liquid Crystal Display), CRT (Cathode Ray Tube), etc. and displays an input instruction from the operation section 23, data, etc. according to an instruction of the display signal input from the control section 21.

The communication section 25 includes a LAN adapter, a router, TA (Terminal Adapter), etc. and controls transmitting and receiving of data between each device connected to the communication network N.

(Configuration of Diagnosis Console 3)

The diagnosis console 3 is a device to display a dynamic image transmitted from the capturing console 2 for a doctor to perform interpretation of the image for diagnosis.

As shown in FIG. 1, the diagnosis console 3 includes a control section 31, a storage section 32, an operation section 33, a display section 34, a communication section 35, etc. and each section is connected by a bus 36.

The control section 31 is composed of a CPU, RAM, etc. According to an operation of the operation section 33, the CPU of the control section 31 reads out a system program or various processing programs stored in the storage section 32 and develops the program in the RAM and centrally controls the operation of each section of the diagnosis console 3 according to the developed program.

The storage section 32 is composed of a nonvolatile semiconductor memory, hard disk, etc. The storage section 32 stores various programs performed by the control section 31, parameter necessary to perform processing by the program, or data such as processing result, etc. The various programs are stored in a form of a readable program code and the control section 31 sequentially performs the operation according to the program code.

The operation section 33 is composed of a keyboard including a cursor key, number input key, various function keys, etc., and a pointing device such as a mouse, etc. and outputs an instruction signal input by operation of the key on the keyboard or operation of the mouse to the control section 31. The operation section 33 can include a touch panel on the display screen of the display section 34, and in this case, the instruction signal input through the touch panel is output to the control section 31.

The display section 34 is composed of a monitor such as an LCD, CRT, etc. and displays an input instruction from the operation section 33, data, etc. according to an instruction of the display signal input from the control section 31.

The communication section 35 includes a LAN adapter, a router, TA, etc. and controls transmitting and receiving of data between each device connected to the communication network N.

(Operation of Dynamic Image Capturing System 100)

Next, the operation of the above dynamic image capturing system 100 is described.

Figure 2:
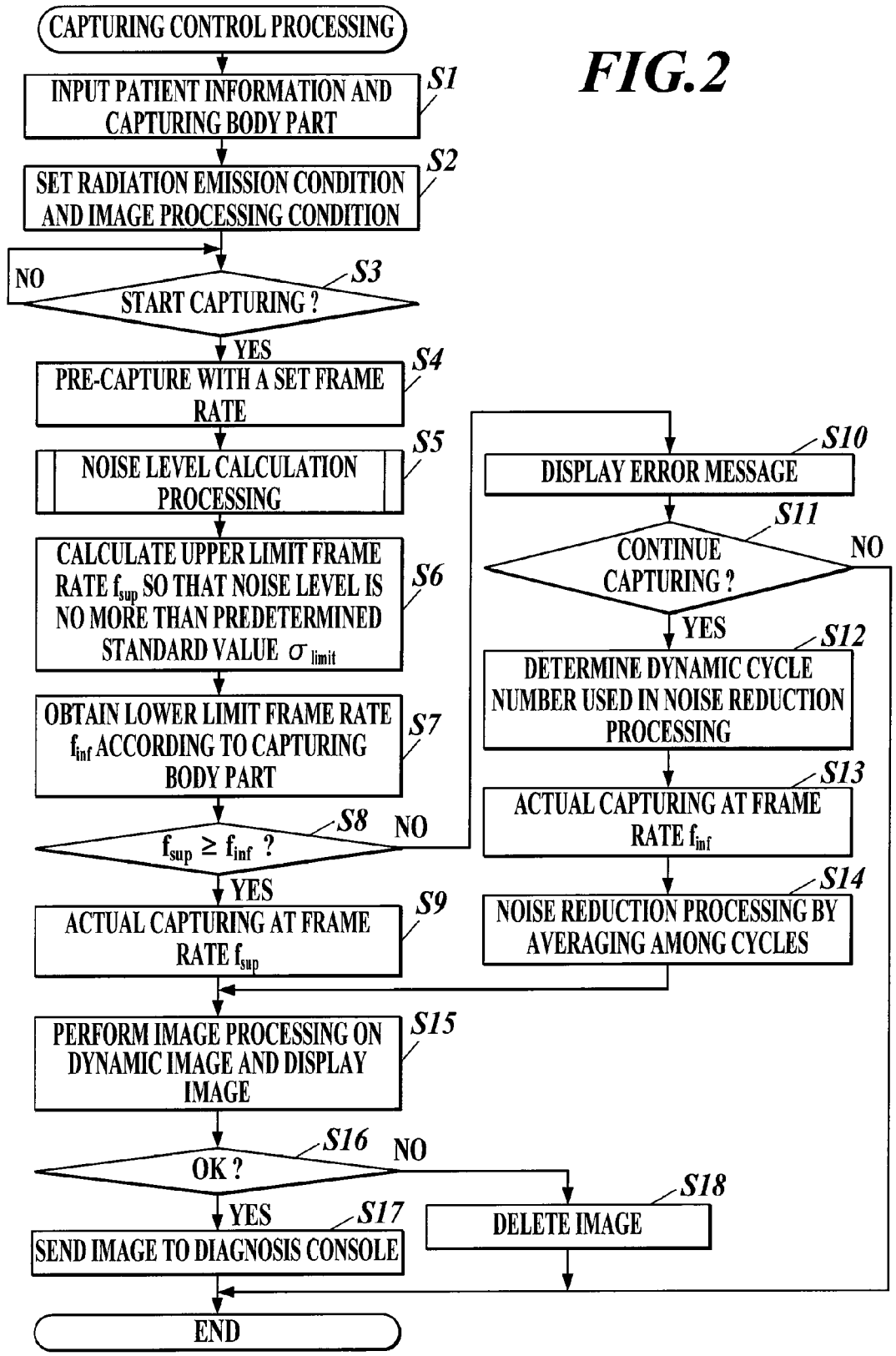
FIG. 2 is a flowchart showing a capturing control processing performed by the control section of the capturing console shown in FIG. 1.

FIG. 2 shows a flow of a capturing control processing performed by the control section 21 of the capturing console 2.

First, input of patient information (name, height, weight, age, sex, etc.) of the patient P, specification input of the capturing body part, etc. are received on the operation section 23 from the capturing operator (step S1).

Next, the radiation emission condition according to the capturing body part specified by the operation section 23 is set on the radiation emission control device 12 and the image reading condition according to the specified capturing body part is set on the reading control device 14 (step S2). In step S2, first, the capturing condition (radiation emission condition and image reading condition) is read out from the storage section 22. Next, necessary capturing condition is calculated based on the read out capturing condition and cycle information of the capturing body part obtained from the cycle detection device 16. Other capturing conditions, for example, pulse width, etc. are calculated so that the emission radiation amount of the total dynamic capturing is no more than the total emission radiation amount set in advance and the calculation is based on, for example, the frame rate (pulse rate) read out from the storage section 22, total emission radiation amount and cycle information of the capturing body part detected by the cycle detection device 16. Then, among the read out capturing condition and calculated capturing condition, the radiation emission condition is set in the radiation emission control device 12 and the image reading condition is set in the reading control device 14.

Next, the apparatus stands by for input of instruction to start capturing by operation of the operation section 23 and when capturing start instruction is input on the operation section 23 (step S3; YES), the capturing instruction is output to the radiation emission control device 12 and the reading control device 14 and pre-capturing of one or a few frames is performed based on the set capturing condition (including frame rate) (step S4). The pre-capturing is capturing performed before the actual dynamic capturing. In the present embodiment, the pre-capturing is performed to obtain a frame image for image analysis in order to perform adjustment of the frame rate of the actual capturing. Then, the noise level calculation processing is performed on the frame image obtained by the capturing (step S5).

Figure 3:
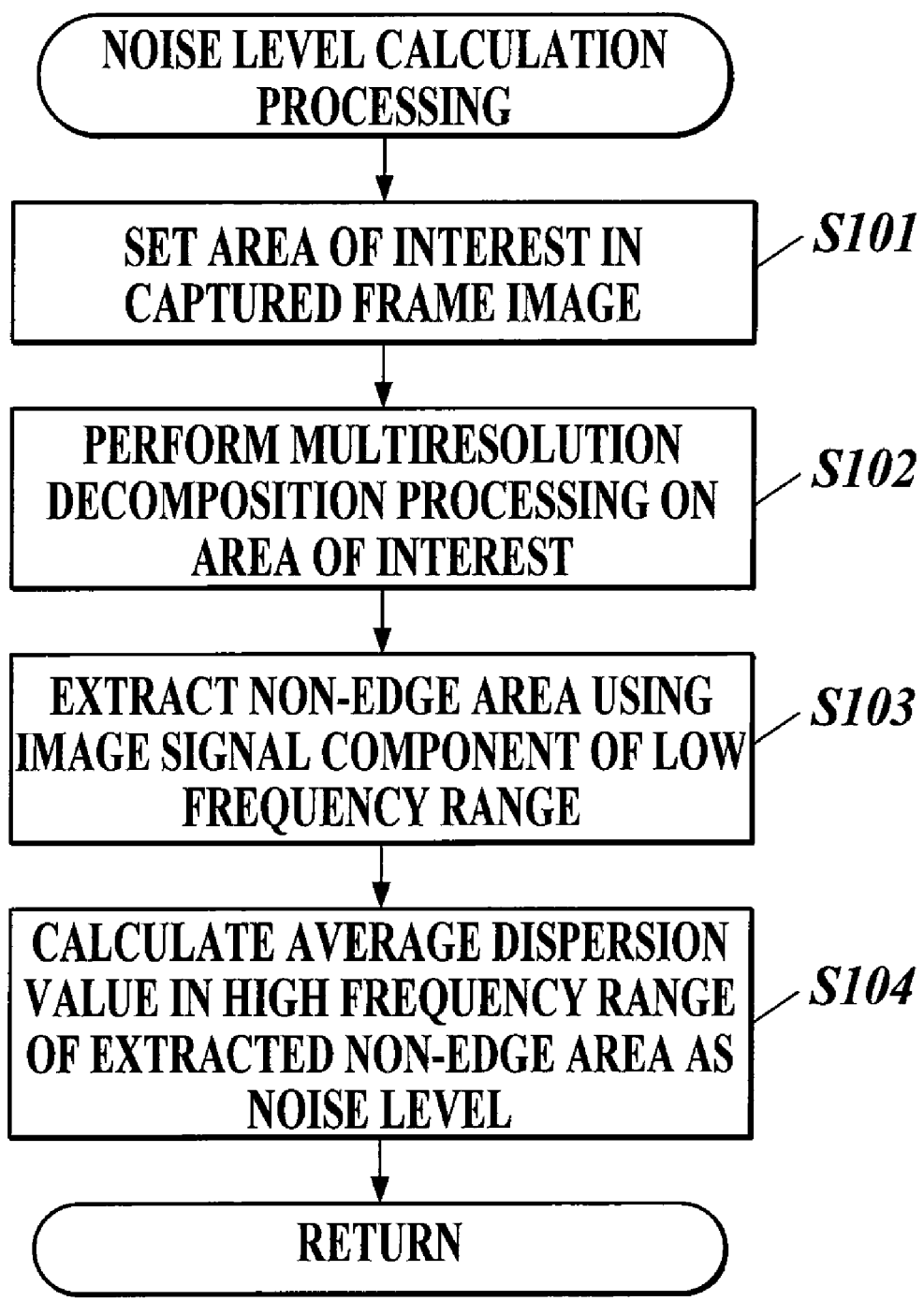
FIG. 3 is a flowchart showing a noise level calculation processing performed in step S5 shown in FIG. 2.

FIG. 3 shows a flow of the noise level calculation processing performed by the control section 21 in step S5 shown in FIG. 2.

First, the area of interest is set on any one of the frame images (frame image F) obtained by the capturing (step S101). The area of interest is determined in advance according to the capturing body part and the area of interest is set in a position according to the capturing body part. Image analysis can be performed on the frame image F to extract an area of interest.

Next, the multiresolution decomposition processing is performed on the image of the area of interest (step S102).

Figure 4:
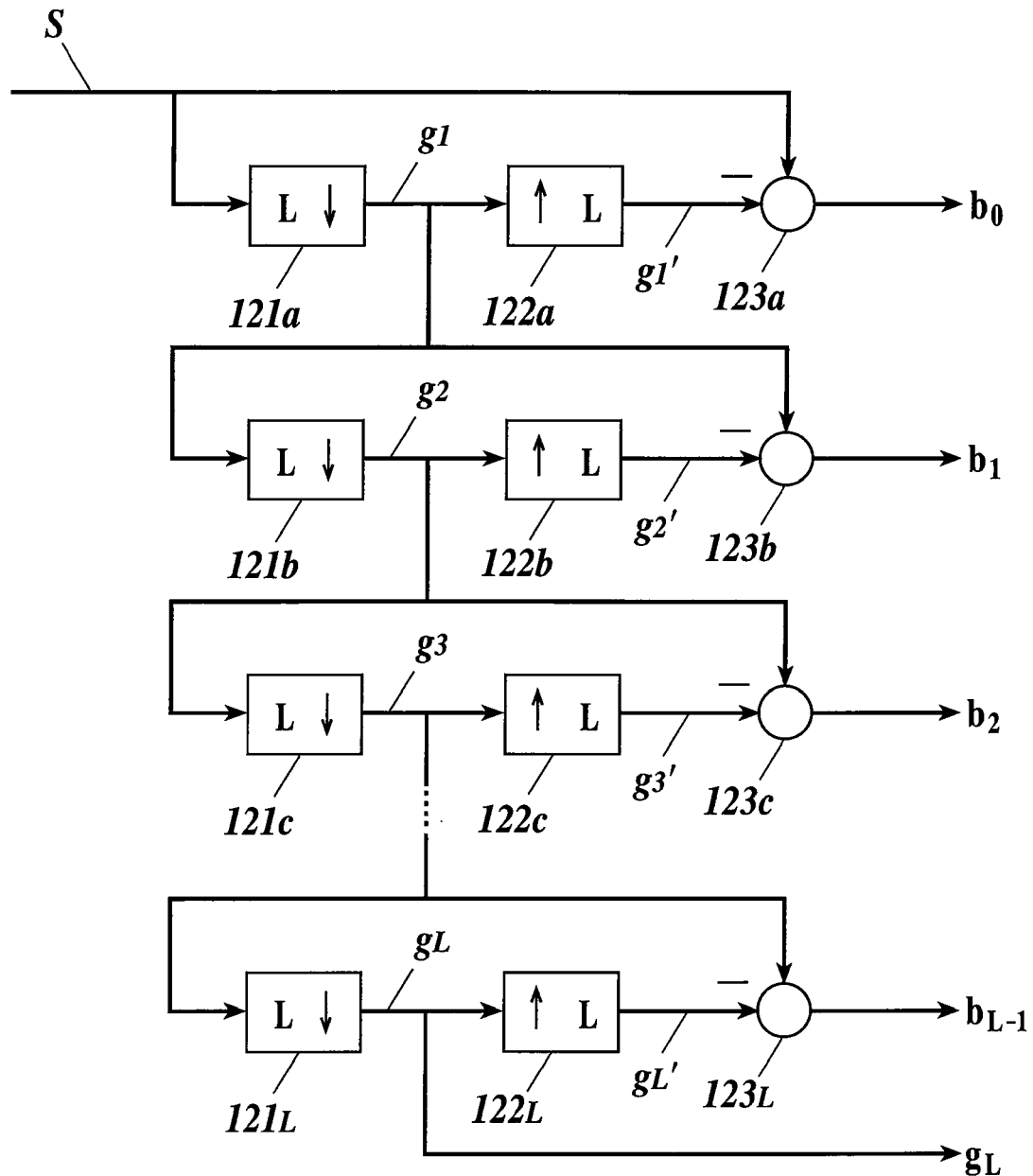
FIG. 4 is a diagram describing multiresolution decomposition processing performed in step S102 shown in FIG. 3.

Here, the multiresolution decomposition processing is described with reference to FIG. 4. In the present embodiment, an example is explained where the multiresolution decomposition is performed on the input image (here, the image of the area of interest) by the Laplacian pyramid method and the input image is decomposed to an image signal component of a plurality of frequency ranges different from each other. According to the Laplacian pyramid method, rapid processing is possible, but other methods such as wavelet transform, etc. can also be used.

First, the image signal of the area of interest (original image signal S) is filtered by the filtering section 121a composing the low pass filter.

The original image signal S filtered by the filtering section 121a is sampled (double sampling) in every other pixel to generate low resolution approximation image g1. The low resolution approximation image g1 is a size of ¼ of the original image.

Next, the interpolation section 122a interpolates a pixel with a value 0 in the interval sampled in the low resolution approximation image g1. The interpolation is performed by inserting a line and column with a value 0 in every column and line of the low resolution approximation image g1. Since the interpolated low resolution approximation image is inserted with a pixel with a value 0 in every other pixel, the change of the signal value is not smooth. After such interpolating is performed, filtering is performed again on the low pass filter included in the interpolating section 122a to obtain low resolution approximation image g1'. The low resolution approximation image g1' is in a state where the change of the signal value is smooth compared to the low resolution approximation image shortly after the above interpolation.

In this low resolution approximation image g1', the interpolation of 0 in every other pixel and filtering is performed after the image is made to ¼ so that the frequency higher than half of the spatial frequency of the original image is cleared.

Then, the subtractor 123a performs subtraction of the low resolution approximation image g1' from the original image to obtain detailed image b0. The subtraction is performed between the corresponding pixels of the original image and the low resolution approximation image g1'. With this, the detailed image b0 is an image showing only the frequency range higher than half of the spatial frequency of the original image. In other words, when the Nyquist frequency is Ny, the detailed image b0 is an image signal component of the frequency range of Ny/2 to Ny.

Further, filtering processing is performed on the low resolution approximation image g1 from the above low pass filter 121a by the low pass filter 121b. With this, the low resolution approximation image g1 is further sampled in every other pixel and converted to low resolution approximation image g2 which is ¼ (1/16 of original). Then, similar processing is performed on the low resolution approximation image g2 by the interpolation section 122b and the subtractor 123b and a detailed image b1 is generated from the low resolution approximation image g2'. In other words, when the Nyquist frequency is Ny, the detailed image b1 is an image signal component of the frequency range Ny/4 to Ny/2.

By sequentially repeating such processing, detailed image bk−1 and remaining image gL is obtained from the low resolution approximation image gk (here, k=1−L) generated by the low pass filter 121.

Here, the detailed image bk−1 is an image where the resolution becomes lower from b0 in order, in other words, the frequency range becomes lower and the detailed image bk−1 is an image signal component of the frequency range of (Ny/2^((k−1)+1)) to (Ny/2^(k−1)).

As described above, with the multiresolution decomposition processing, the image signal of the area of interest is decomposed to an image signal component of a plurality of frequency ranges.

Figure 5A:
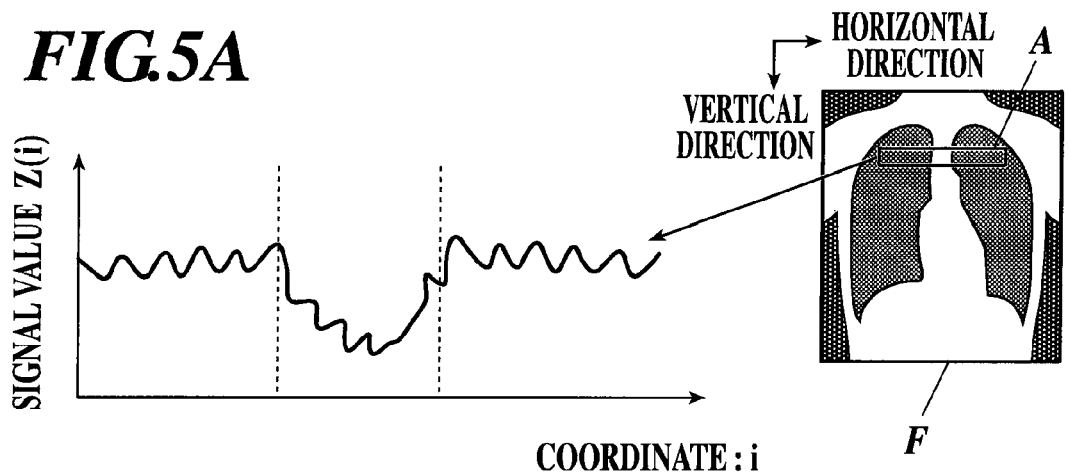
FIG. 5A is a diagram showing a signal value of each pixel (showing pixel position with coordinate (i)) in an area of interest before performing multiresolution decomposition processing.
Figure 5B:
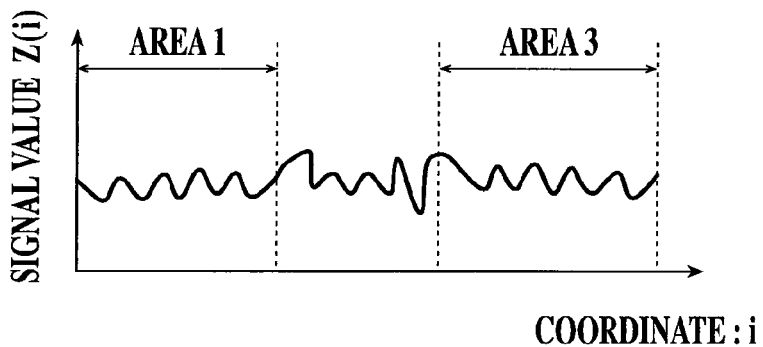
FIG. 5B is a diagram showing an image signal component of a high frequency range among image signal components of a plurality of frequency ranges obtained as a result of the multiresolution decomposition processing on FIG. 5A.
Figure 5C:
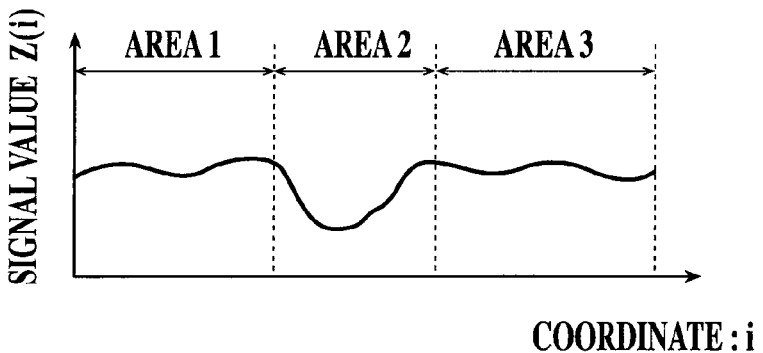
FIG. 5C is a diagram showing an image signal component of a low frequency range among image signal components of a plurality of frequency ranges obtained as a result of the multiresolution decomposition processing on FIG. 5A.

FIG. 5A to FIG. 5C schematically show a signal value of each pixel in an area of interest before performing the above multiresolution decomposition processing and a signal value of the image signal component of the plurality of frequency ranges obtained by performing the multiresolution decomposition processing.

FIG. 5A is a diagram showing a signal value of each pixel (coordinate (i) shows pixel position) in an area of interest before performing the multiresolution decomposition processing. FIG. 5B is a diagram showing an image signal component (for example detailed image b0) of a high frequency range among the image signal component of the plurality of frequency ranges obtained as a result of the multiresolution decomposition processing performed on FIG. 5A. FIG. 5C is a diagram showing an image signal component (for example, detailed image bL−1) of a low frequency range among the image signal component of the plurality of frequency ranges obtained as a result of the multiresolution decomposition processing performed on FIG. 5A.

To simplify description, in the description below, the area of interest set in step S101 is a one dimensional area extending in a horizontal direction as shown in area A shown in FIG. 5A, however, the area may be a two dimensional area.

After the multiresolution decomposition processing is finished, the processing result is used to calculate the noise level $\sigma_N$ of the frame image F by the processing of step S103 and S104.

Here, in an image area where there is no outline of the structural object (non-edge area), the dispersion value of the image signal component of the low frequency range and the dispersion value of the image signal component of the high frequency range should show a low value. However, when there is noise in the area, the dispersion value of the image signal component of the high frequency range become high. Therefore, in the present embodiment, the average dispersion value of the image signal component of the high frequency range in the non-edge area of the area of interest is calculated as the noise level $\sigma_N$ of the frame image F. The noise level $\sigma_N$ is an index value showing image quality. A higher noise level $\sigma_N$ shows the image quality is bad.

Below, the calculation of the noise level $\sigma_N$ is described.

First, the non-edge area is extracted using the image signal component of the low frequency range (step S103).

The non-edge area can be extracted by performing the following (1)-(2) below.

(1) The area of interest is divided into local areas with respect to n pixels (n is a positive number determined in advance) and the dispersion value $\sigma$ is calculated with respect to each local area.

Figure 6:
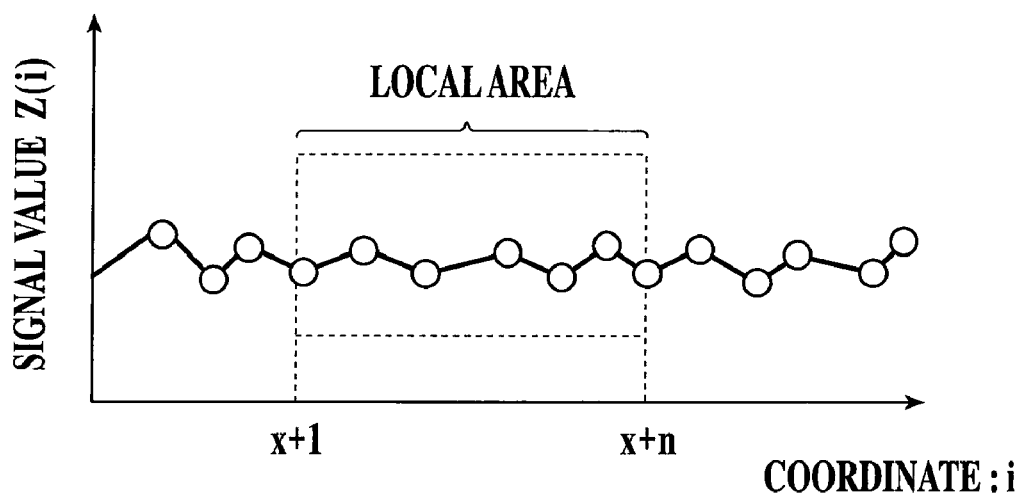
FIG. 6 is a diagram describing a local area.

For example, the dispersion value (local dispersion value) $\sigma$ in a local area of coordinate i=x+1 to x+n shown in FIG. 6 can be obtained by the formula shown in [Formula 1].

$$\sigma^2 = \frac{1}{n} \sum_{i=x+1}^{x+n} \{Ave - Z(i)\}^2 \qquad \text{[Formula 1]}$$

Ave shows the average value of the signal value of each pixel in the local area.

(2) Next, the dispersion value $\sigma$ in each local area and the threshold $\sigma_{mid}$ determined in advance is compared and the local area where $\sigma < \sigma_{mid}$ is extracted as the non-edge area.

For example, in FIG. 5C, area 1 and area 3 are extracted as non-edge areas. As $\sigma_{mid}$, for example, a value calculated from the [Formula 2] below can be used but is not limited to this.

$$\sigma_{mid} = \sigma\sqrt{2\ln(n)} \qquad \text{[Formula 2]}$$

In [Formula 2], $\sigma$ is a dispersion value of the entire area of interest in the low frequency range and n is a pixel number.

After the non-edge area is extracted, the average dispersion value of the image signal component in the area (for example, area 1 and area 3 shown in FIG. 5B) of the high frequency range corresponding to the extracted non-edge area is calculated as the noise level $\sigma_n$ (step S104).

Specifically, first the dispersion value $\sigma_{supt}$ (t=1 to N (N is a number of the non-edge area) with respect to each extracted non-edge area is calculated. The dispersion value $\sigma_{supt}$ can be calculated by a similar formula to the formula shown in [Formula 1]. Next, the average dispersion value (noise level $\sigma_N$) of N areas of the non-edge area is calculated. The formula to calculate the noise level $\sigma_N$ is as shown in [Formula 3].

$$\sigma_N = \frac{1}{N} \sum_{t=1}^{N} \sigma_{supt} \quad \text{[Formula 3]}$$

After the noise level $\sigma_N$ is calculated, the processing advances to step S6 shown in FIG. 2.

Figure 7:
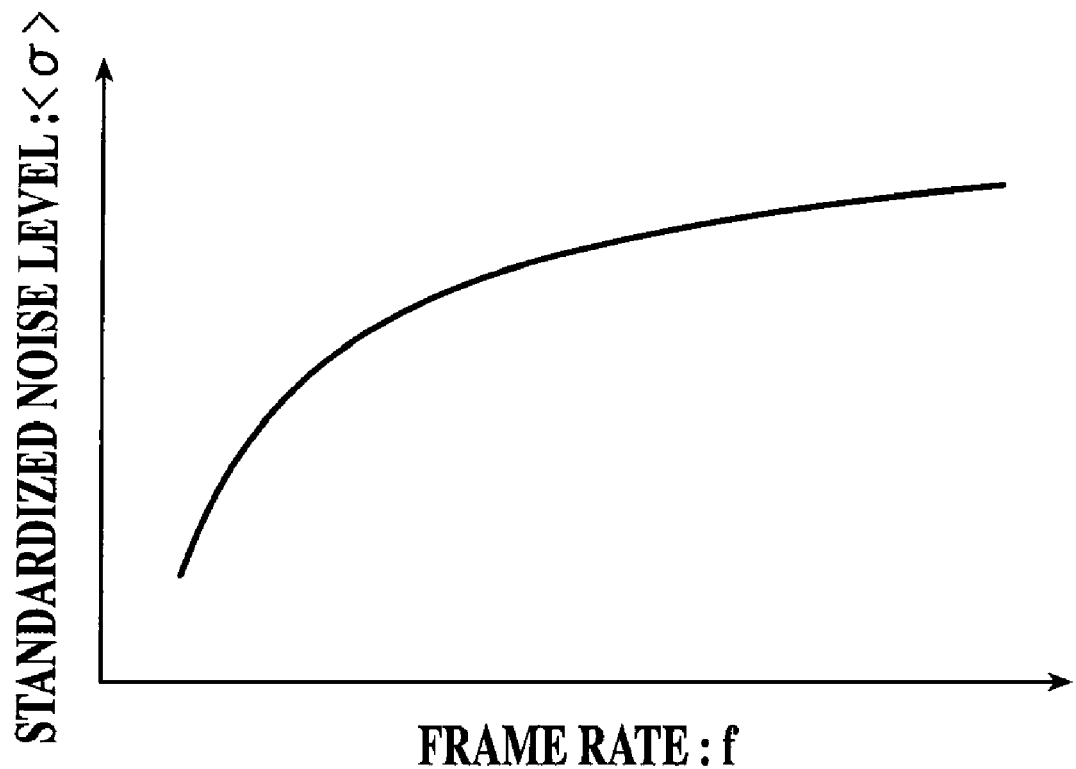
FIG. 7 is a diagram showing a relation between normalized noise level and frame rate.

In step S6 shown in FIG. 2, the upper limit frame rate $f_{sup}$ is calculated so that the noise level of the frame image obtained by dynamic capturing is no more than a predetermined standard value $\sigma_{limit}$ based on the calculated noise level $\sigma_N$ and the relational formula between the standardized noise level and the frame rate shown in FIG. 7 and [Formula 4], and the result is notified to the capturing operator by display, etc. on the display section 24 (step S6).

$$<\sigma(f)> \propto \sqrt{f} \quad \text{[Formula 4]}$$

Here, the total emission radiation amount of one dynamic capturing is determined in advance with respect to each capturing body part, and the control section 21 controls the emission radiation amount with respect to each frame image based on the total emission radiation amount. In other words, when the frame rate is raised, the emission radiation amount with respect to each frame image is reduced. This is to suppress the amount of exposure in the total dynamic capturing of the capturing body part as an object. Therefore, when the frame rate is raised, the noise level with respect to each frame image becomes high. The standard value $\sigma_{limit}$ determined in advance is a value obtained experimentally and empirically as a noise level allowable in diagnosis. In step S6, the upper limit of the frame rate $f_{sup}$ where the noise level is no more than the $\sigma_{limit}$ is calculated. As $\sigma_{limit}$, for example the value calculated from the formula shown in the above [Formula 2] can be used, but is not limited to this.

As shown in FIG. 7 and the formula shown in [Formula 4], when the noise level of the frame rate f1 used in capturing of the frame image F is $\sigma_N$, $f_{sup}$ can be obtained by the formula shown in [Formula 5].

$$f_{sup} = \left(\frac{\sigma_{limit}}{\sigma_N}\right)^2 f_1 \quad \text{[Formula 5]}$$

Next, the lower limit frame rate $f_{inf}$ determined in advance according to the capturing body part is read out from the storage section 22 and the lower limit frame rate $f_{inf}$ is obtained (step S7). As described above, the lower limit frame rate $f_{inf}$ is a frame rate set as the lower limit necessary for diagnosis of the dynamic state of the capturing body part. For example, when the capturing body part is the heart and a dynamic image of the heart rate cycle captured with a temporal resolution of 10% or more is necessary for diagnosis, when the heart rate is 60 times/minute, $f_{inf}>10$ frames/second.

In the present embodiment, the lower limit frame rate $f_{inf}$ is stored in advance in the storage section 22, however, the lower limit frame rate $f_{inf}$ can be calculated in the control section 21 based on the time necessary for one dynamic cycle of the capturing body part obtained by the cycle detection device 16 and the number of frame images with respect to each unit of time necessary for diagnosis.

Next, the calculated upper limit frame rate $f_{sup}$ and the lower limit $f_{inf}$ are compared and when $f_{sup} \geq f_{inf}$ (step S8; YES), the frame rate is determined to $f_{sup}$ and set in the radiation emission control device 12 and the actual dynamic capturing is performed with the frame rate $f_{sup}$ (step S9). In step S9, other capturing condition such as the pulse width, etc. is changed based on the frame rate $f_{sup}$ so that the total emission radiation amount in the actual capturing matches the total emission radiation amount set in advance. Then, the changed capturing condition is set in the radiation emission control device 12 and the reading control device 14 and control is performed so that the actual capturing is performed with the changed capturing condition. In the present embodiment, the frame rate in the following capturing is determined as frame rate $f_{sup}$, but any frame rate which is no more than $f_{sup}$ and no less than $f_{inf}$ can be determined. By setting the frame rate to $f_{sup}$, a dynamic image which reproduces the movement of the capturing body part most finely within the range of the acceptable noise level can be obtained.

The frame image obtained by capturing is sequentially input to the capturing console 2. When the cycle detection apparatus 16 detects the predetermined number of capturing cycles of the dynamic cycles after capturing starts with the frame rate $f_{sup}$, the instruction to end capturing is output to the radiation emission control device 12 and the reading control device 14, and the capturing operation stops. After the capturing ends, the processing advances to step S15.

Alternatively, when $f_{sup}<f_{inf}$ (step S8; NO), an error message is displayed on the display section 24 as a notification section and it is notified that $f_{sup}<f_{inf}$, etc. to the capturing operator who is the user (step S10).

Here, when the frame rate used in the capturing is less than the lower limit frame rate $f_{inf}$ necessary for diagnosis, the dynamic image obtained by the capturing does not represent the movement of the capturing body part enough to be used in diagnosis. Therefore, when capturing is continued at $f_{sup}<f_{inf}$, the actual capturing is performed with $f_{inf}$. However, when capturing is performed with $f_{inf}$, the noise level of the dynamic image obtained by the actual capturing becomes higher than the acceptable noise level $\sigma_{limit}$. Therefore, it is displayed on the display section 24 that $f_{sup}<f_{inf}$ if capturing is continued, that the actual capturing is performed at frame rate $f_{inf}$, and that the noise level of the image obtained by the actual capturing is less than the acceptable level and thus noise reduction processing is performed, etc. Also, a "capturing continue" button for the user to input instruction to continue capturing and a "capturing cancel" button for the user to input instruction to cancel capturing are displayed. The user operates any of the buttons on the operation section 23.

When the "capturing cancel" button is pressed on the operation section 23 (step S11; NO), the processing ends.

Alternatively, when the "capturing continue" button is pressed on the operation section 23 (step S11; YES), a dynamic cycle number M of the dynamic image used in noise reduction processing by averaging between cycles is calculated (step S12).

Here, the noise reduction processing by averaging between cycles is described.

Figure 8:
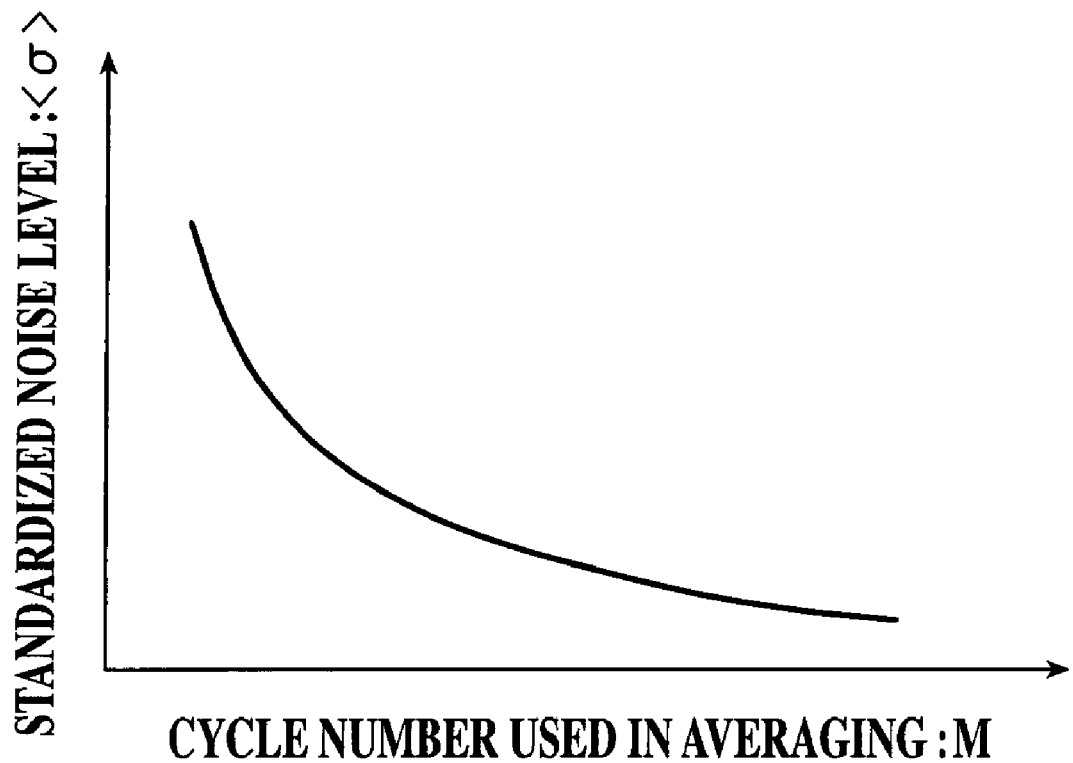
FIG. 8 is a diagram showing a relation between a normalized noise level and a cycle number used in averaging.

When a plurality of cycles of a dynamic state with a cyclic nature is captured with a certain frame rate, a state (size, position, etc.) of the capturing body part captured n-th in each cycle is substantially the same state. Also, when the signal values of the pixels in corresponding positions of frame images of M cycles are averaged, it is known that the noise level is reduced to almost $1/\sqrt{M}$ as shown in FIG. 8. Therefore, in the present embodiment, the dynamic cycle number M is calculated so that the noise level is $\sigma_{limit}$ when captured with lower limit frame rate $f_{inf}$ and the dynamic capturing of M cycles is performed. Then, an image is formed where the signal values of the corresponding pixels in the frame images captured n-th in each cycle of M cycles are averaged to perform noise reduction processing.

Specifically, in step S12, the noise level $\sigma_N$ of frame rate $f_{inf}$ is calculated based on the noise level calculated from the frame image F in step S5 shown in FIG. 2 and the relational formula between the standardized noise level and the frame rate shown in [Formula 4] and FIG. 7. Then, the dynamic cycle number M is calculated so that the noise level is no more than the above $\sigma_{limit}$ based on the calculated noise level $\sigma_N$ and relational formula between standardized noise level and the cycle number used in averaging shown in FIG. 8. The dynamic cycle number M can be calculated by the [Formula 6] shown below.

$$M = \left(\frac{\sigma_N}{\sigma_{limit}}\right)^2 \quad \text{[Formula 6]}$$

Also, the frame rate of the dynamic capturing is determined to $f_{inf}$ and set in the radiation emission control device 12 and the actual capturing of the frame rate $f_{inf}$ starts (step S13). In step S13, other capturing condition such as pulse width, etc. is changed so that the total emission radiation amount in the actual capturing is the predetermined total emission radiation amount based on the frame rate $f_{inf}$. Then, the changed capturing condition is set in the radiation emission control device 12 and the reading control device 14 and control is performed so that the capturing is performed with the changed capturing condition.

The image data of each frame image obtained by the capturing is sequentially input to the capturing console 2. When the cycle detection device 16 detects the dynamic state of the calculated capturing cycle number to be captured and detects the predetermined number of capturing cycles of the dynamic cycles after capturing starts with the frame rate $f_{inf}$, the instruction to end capturing is output to the radiation emission control device 12 and the reading control device 14, and the capturing operation stops.

Figure 9:
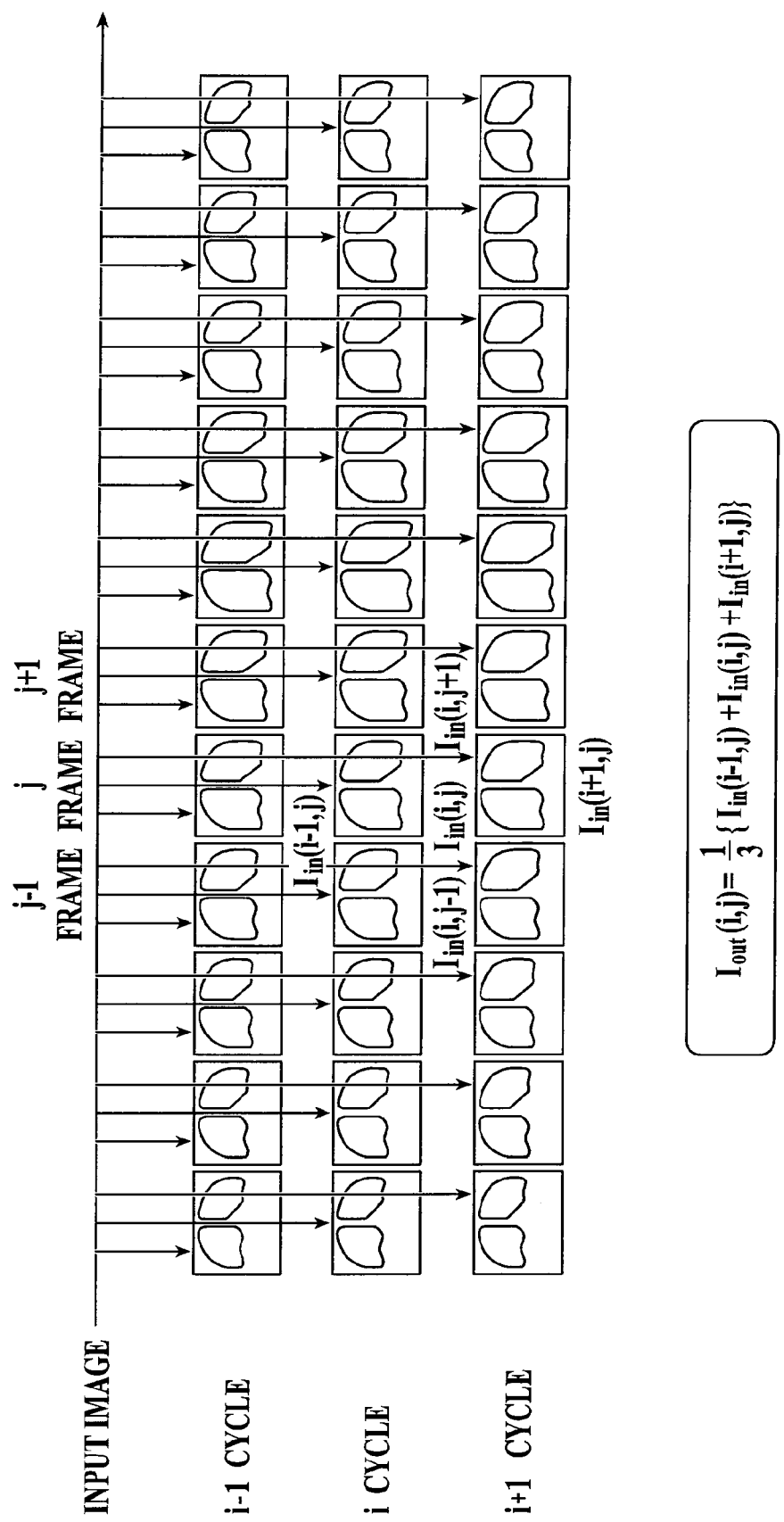
FIG. 9 is a diagram explaining noise reduction processing by averaging between cycles when the number of dynamic cycles used in averaging is 3.

When the capturing ends, the noise reduction processing by averaging between cycles is performed (step S14). In the noise reduction processing by averaging between cycles the signal values of the corresponding pixels among the frame images captured n-th in each cycle of M cycles are averaged. FIG. 9 shows an example of noise reduction processing when the dynamic cycle number M is 3. As shown in FIG. 9, for example, the frame image $I_{out}$ of the j-th frame of the i-th cycle is obtained by adding the signal values of each pixel corresponding to the j-th frame of the i−1-th cycle, i-th cycle and i+1-th cycle and dividing by the capturing cycle number 3. In FIG. 9, an example of simple averaging is described, but a weight can be added among the averaged cycles and weighted averaging can be performed. After the noise reduction processing ends, the processing advances to step S15.

In step S15, image processing such as density correction is performed on the frame image obtained by the actual capturing and then the image is stored in the storage section 22 corresponded with number showing order of capturing and displayed on the display section 24 (step S15). The capturing operator confirms the positioning, image quality, etc. of the displayed dynamic image and judges whether or not an image suitable for diagnosis is obtained by the actual capturing (capturing OK) or another capturing is necessary (capturing NG). Then, the operation section 23 is operated to input the judgment result.

After the judgment result showing capturing OK is input by a predetermined operation on the operation section 23 (step S16; YES), information such as identification ID to identify the dynamic image, patient information, capturing body part, radiation emission condition, image reading condition, number showing order of capturing, cycle information, whether or not noise reduction processing is performed, etc. is added (for example, writing in a header area of the image data by DICOM format) on each of the series of frame images obtained in the actual dynamic capturing and the image is transmitted to the diagnosis console 3 through the communication section 25 (step S17). Then, the processing ends. Alternatively, when the judging result showing the capturing NG is input by predetermined operation of the operation section 23 (step S16; NO), the series of frame images stored in the storage section 22 is deleted (step S18) and the processing ends.

In the diagnosis console 3, when the series of frame images of the dynamic image is received from the capturing console 2 by the communication section 35, the control section 31 stores the received frame images in the storage section 32.

On the diagnosis console 3, the identification ID, etc. is input on the operation section 33, and when the dynamic image which is the object of diagnosis is specified, the control section 31 reads out the series of frame images of the specified dynamic image from the storage section 32. Then, the images are sequentially displayed on the display section 34 to be interpreted and diagnosed by the doctor.

As described above, according to the dynamic image capturing system 100, the control section 21 of the capturing console 2 analyzes at least one of the frame images obtained by the pre-capturing and calculates the index value showing the image quality. Then, based on the index value showing the calculated image quality, the control section 21 of the capturing console 2 calculates the upper limit frame rate $f_{sup}$ where the index value showing the image quality of the frame image obtained by the actual dynamic capturing is no more than a standard value set in advance. Then, based on the calculated upper limit frame rate $f_{sup}$ and the lower limit frame rate $f_{inf}$ which is the necessary lower limit to diagnose the dynamic state of the capturing body part, the frame rate used in the dynamic capturing is determined and the capturing is performed at the frame rate determined in capturing device 1.

Therefore, a dynamic image with image quality demanded in diagnosis can be obtained without increasing the exposure amount of the object.

The index value showing the image quality calculated by the control section 21 is the noise level and the control section 21 calculates the upper limit frame rate $f_{sup}$ so that the noise level is no more than the standard value set in advance. Then, the control section 21 determines the frame rate based on the calculated upper limit frame rate $f_{sup}$ and allows the capturing device 1 to perform the dynamic capturing. Therefore, a dynamic image with image quality where the noise level is no more than the level acceptable in diagnosis can be obtained.

Also, the control section 21 compares the upper limit frame rate $f_{sup}$ and the lower limit frame rate $f_{inf}$ which is the necessary lower limit to diagnose the dynamic state of the capturing body part and when $f_{sup} < f_{inf}$, this is displayed on the display section 24, and the capturing operator is able to know that the dynamic image obtained by the dynamic capturing is not suitable for diagnosis as is.

Also, even when $f_{sup} < f_{inf}$ and the instruction to continue capturing is input on the operation section 23, the frame image when the actual capturing is performed at the lower limit frame rate $f_{inf}$ is averaged among the cycles to determine the dynamic cycle number M where the noise level is no more than the standard value set in advance, and the noise reduction processing is performed by performing the averaging of the pixel signal values among the frame images of the cycle number M of the actual capturing at the lower limit frame rate $f_{inf}$. Therefore, with the noise reduction processing, the dynamic image with the image quality no more than the noise level acceptable for diagnosis can be obtained.

The description of the above described embodiment is one example of a preferable dynamic image capturing system of the present invention and the present invention is not limited to the above.

For example, in the present embodiment, it is described to use a noise level calculated from the dispersion value as an index value to show the image quality, however, the value is not limited to this, and for example, an entropy value can be used.

As the description of the entropy value, when the entropy value is smaller than a predetermined value in a middle frequency range and the entropy value is large in the highest frequency range in a certain area, it can be said that the noise component is dominant in that area.

The entropy value Se in a local area of coordinate i=x+1 to x+n as shown in FIG. 6 can be obtained by the following formula of [Formula 7].

$$Se = -\sum_{z=0}^{m-1} P(z)\log_2\{p(z)\}$$ [Formula 7]

Here, m represents the tone number and P(z) represents the probability that the pixel in the area will have a pixel value (signal value) "z".

The capturing control processing when the entropy value is used is substantially similar to the processing shown in FIG. 2. First, multiresolution decomposition is performed on the captured frame image. Next, an area where the entropy value is smaller than the predetermined value in a middle frequency range is extracted and the entropy value (average) of the extracted area in the highest frequency range is calculated. Then, the upper limit frame rate is determined as $f_{sup}$ so that the entropy value is no more than a predetermined value based on the calculated entropy value and a predetermined relational formula between the standardized entropy value and the frame rate. When the dynamic cycle number M used in the noise reduction processing by averaging is calculated, the capturing cycle number is determined based on the predetermined relational formula between the standardized entropy value and the dynamic cycle number M used in averaging.

Figure 10:
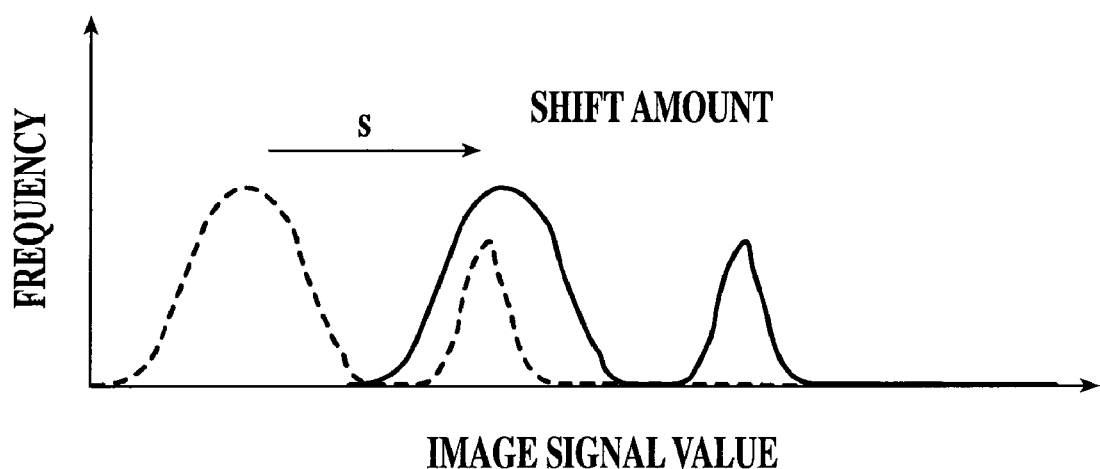
FIG. 10 is a diagram explaining shift amount of a density histogram.

Also, as for the image obtained by capturing, a density histogram is made and density correction is performed by shifting the density histogram so that a predetermined density (for example, highest density, etc.) is a density value determined in advance. Therefore, a shift amount s of the density histogram is obtained from the image of a frame captured in the beginning (see FIG. 10) and the shift amount s can be used as the index value to show the image quality. The larger the shift value s is, the farther it is from the standard density value, and therefore, the larger the shift amount s is, this shows the image quality is bad.

In capturing control processing where the shift amount s is used, first a density histogram is formed from a captured frame image and the shift amount s is calculated. Next, the upper limit frame rate $f_{sup}$ is determined so that the shift amount is no more than a predetermined value based on the calculated shift amount s and a predetermined relational formula between the standardized shift amount of the density histogram and the frame rate. When the dynamic cycle number M used in the noise reduction processing by averaging is calculated, the dynamic cycle number M is determined based on the predetermined relational formula between the standardized shift amount of the density histogram and the capturing cycle number used in averaging.

Also, in the above description, an example is disclosed where a hard disk, semiconductor nonvolatile memory, etc. is used as a computer readable medium of the program of the present invention, however, the invention is not limited to the above. As other computer readable medium, a portable recording medium such as a CD-ROM, etc. can be applied. Also, as a medium to provide the data of the program of the present invention through a communication line, a carrier wave can be applied.

Other detailed configuration and detailed operation of each device of the dynamic image capturing system 100 can be suitably modified without leaving the scope of the present invention.

The entire contents including specification, claims, drawings and abstract of Japanese Patent Application No. 2008-126634 filed on May 14, 2008 to the Japanese Patent Office are incorporated herein by reference.

INDUSTRIAL APPLICABILITY

The present invention can be used in the field of medicine in a dynamic image capturing system to capture a dynamic image of a patient.

DESCRIPTION OF REFERENCE NUMERALS

100 dynamic image capturing system
1 capturing device
11 radiation source
12 radiation emission control device
13 radiation detection section
14 reading control device
15 cycle detection sensor
16 cycle detection device
2 capturing console
21 control section
22 storage section
23 operation section
24 display section
25 communication section
26 bus
3 diagnosis console
31 control section
32 storage section
33 operation section
34 display section
35 communication section
36 bus

The invention claimed is:

1. A dynamic image capturing control apparatus connected to a capturing apparatus in which dynamic capturing is performed by successively emitting radiation on a capturing body part a plurality of times to obtain a plurality of frame images showing a dynamic state of the capturing body part, the dynamic image capturing control apparatus comprising:
an operation section to specify the capturing body part which is to be a capturing object;
a capturing control section to set in the capturing apparatus a capturing condition including emission radiation amount and frame rate used in the dynamic capturing according to the capturing body part specified by the operation section to perform the dynamic capturing to obtain a plurality of frame images showing the dynamic state of the capturing body part;

an index value calculation section to analyze at least one frame image obtained by the capturing device before the actual dynamic capturing to calculate an index value showing image quality;

an upper limit frame rate calculation section to calculate an upper limit of the frame rate so that the index value showing image quality of the each frame image obtained by the actual dynamic capturing is no more than a predetermined standard value based on the calculated index value showing the image quality, wherein the capturing control section determines the frame rate to be used in the actual dynamic capturing based on the calculated upper limit frame rate and allows the capturing apparatus to perform the actual dynamic capturing at the determined frame rate.

2. The dynamic image capturing control apparatus of claim 1, wherein the index value showing the image quality is a noise level of the frame image;

the index value calculating section sets an area of interest in the frame image obtained by the capturing device, extracts a non-edge area in the area of interest and calculates a local dispersion value of an image signal component of a high frequency range in the extracted non-edge area to calculate the noise level of the frame image.

3. The dynamic image capturing control apparatus of claim 1, further comprising:

a storage section to store a lower limit frame rate necessary for diagnosis of the dynamic state of the capturing body part with respect to each capturing body part; and a notification section to read out the lower limit frame rate according to the capturing body part specified on the operation section from the storage section to compare the calculated upper limit frame rate to the read out lower limit frame rate and to notify the result when the upper limit frame rate is lower than the lower limit frame rate as a result of the comparison.

4. The dynamic image capturing control apparatus of claim 1, wherein the dynamic state of the capturing body part is a dynamic state with a cyclic nature; and the capturing control section allows the capturing apparatus to perform the actual dynamic capturing at the lower limit frame rate when the upper limit frame rate is lower than the lower limit frame rate, and the dynamic image capturing control apparatus further comprises a noise reduction processing section to perform noise reduction processing by performing averaging of pixel signal values among frame images of a plurality of cycles of the dynamic state of the capturing body part obtained by the actual capturing.

5. The dynamic image capturing control apparatus of claim 4, further comprising a cycle number determination section to calculate tie index value showing image quality of the frame image obtained by performing the dynamic capturing at the lower limit frame rate and to determine a dynamic cycle number of the body part used in the noise reduction processing based on the calculated index value showing the image quality, wherein the noise reduction processing section performs noise reduction processing by performing averaging of pixel signal values among frame images of the determined dynamic cycle number among a plurality of frame images obtained by the actual capturing.

6. A dynamic image capturing system comprising:

an operation section to specify the capturing body part which is to be a capturing object;

a capturing section to perform dynamic capturing by successively emitting radiation on the specified capturing body part a plurality of times to obtain a plurality of frame images showing a dynamic state of the capturing body part;

a capturing control section to set in the capturing section a capturing condition including emission radiation amount and frame rate used in the dynamic capturing according to the capturing body part specified by the operation section to perform the dynamic capturing;

an index value calculation section to analyze at least one frame image obtained by the capturing device before the actual dynamic capturing to calculate an index value showing image quality;

an upper limit frame rate calculation section to calculate an upper limit of the frame rate so that the index value showing image quality of the each frame image obtained by the actual dynamic capturing is no more than a predetermined standard value based on the calculated index value showing the image quality, wherein the capturing control section determines the frame rate to be used in the actual dynamic capturing based on the calculated upper limit frame rate and allows the capturing section to perform the actual dynamic capturing at the determined frame rate.

* * * * *